(12) United States Patent
Demirdjian et al.

(10) Patent No.: US 11,307,209 B2
(45) Date of Patent: Apr. 19, 2022

(54) METHOD DIAGNOSIS OF A PRENATAL DISORDER BY SELECTIVE DETERMINATION OF PLACENTAL GROWTH FACTOR 2

(71) Applicant: CÉZANNE S.A.S., Nimes (FR)

(72) Inventors: Gaïané Demirdjian, Marseilles (FR); Delphine Espinasse, Generac (FR)

(73) Assignee: CÉZANNE S.A.S., Nimes (FR)

( * ) Notice: Subject to any disclaimer, the term of this patent is extended or adjusted under 35 U.S.C. 154(b) by 0 days.

(21) Appl. No.: 15/100,226

(22) PCT Filed: Dec. 3, 2014

(86) PCT No.: PCT/EP2014/076413
§ 371 (c)(1),
(2) Date: May 27, 2016

(87) PCT Pub. No.: WO2015/082545
PCT Pub. Date: Jun. 11, 2015

(65) Prior Publication Data
US 2017/0003304 A1 Jan. 5, 2017

(30) Foreign Application Priority Data

Dec. 3, 2013 (EP) .................................... 13195570

(51) Int. Cl.
| | |
|---|---|
| *G01N 33/53* | (2006.01) |
| *G01N 33/74* | (2006.01) |
| *G01N 33/68* | (2006.01) |
| *C07K 16/22* | (2006.01) |

(52) U.S. Cl.
CPC ............ *G01N 33/74* (2013.01); *C07K 16/22* (2013.01); *G01N 33/689* (2013.01); *C07K 2317/14* (2013.01); *G01N 2800/368* (2013.01)

(58) Field of Classification Search
None
See application file for complete search history.

(56) References Cited

U.S. PATENT DOCUMENTS

| | | |
|---|---|---|
| 2007/0191273 A1 | 8/2007 | Krishna et al. |
| 2009/0176247 A1 | 7/2009 | Bashirians |

FOREIGN PATENT DOCUMENTS

| | | |
|---|---|---|
| WO | 2010059952 A1 | 5/2010 |
| WO | 2010122231 A1 | 10/2010 |

OTHER PUBLICATIONS

Sibiude et al. PLoS ONE 7(11): e50208. doi: 10.1371/jounal.pone. 0050208. Nov. 28, 2012.*

International Search Report and Written Opinion of the International Searching Authority dated Mar. 19, 2015, issued in PCT/EP2014/076413.
Wei, Liu et al., "Relationship between placenta growth factor and the pathogenesis of pregnancy induced hypertension syndrome", Chinese Journal of Obstetrics and Gynecology, Jan. 2001, vol. 36, No. 1.
Cho, Gyeong et al., "Differential Expression of Placenta Growth Factors and Their Recepors in the Normal and Pregnancy-Induced Hypertensive Human Placentas", Journal of Korean Medical Science, Jun. 1, 2003, pp. 402-408, vol. 18, No. 3.
Hauser, Stefanie et al., "A Heparin-Bind Form of Placenta Growth Factor (PIGF-2) is Expressed in Human Umbilical Vein Endothelial Cells and in Placenta", Growth Factors, 1993, pp. 259-268, vol. 9.
Cai, Jun et al., "Placenta Growth Factor-1 Exerts Time-Dependent Stabilization of Adherens Junctions Following VEGF induced Vascular Permeability", PLOS One, Mar. 2011, pp. 1-16, vol. 6, No. 3.
Hoffmann, Daniel C. et al., "Proteolytic Processing Regulates Placental Growth Factor Activities", The Journal of Biological Chemistry, Jun. 2, 2013, pp. 17976-17989, vol. 288, No. 25.
Akolekar, R. et al., "Maternal serum placental growth factor at 11 + 0 to 13 + 6 weeks of gestation in the prediction of pre-eclampsia", Ultrasound in Obstetrics and Gynecology, 2008, pp. 732-739, vol. 32.
Bindra, R. et al., "One-stop clinic for assessment of risk for trisomy 21 at 11-14 weeks: a prospective study of 15 030 pregnancies", Ultrasound in Obstetrics and Gynecology, 2002, pp. 219-225, vol. 20.
Bird, Robert E. et al., "Single-Chain Antigen-Binding Proteins", Science, Oct. 21, 1988, pp. 423-426, vol. 242.
Conde-Agudelo, Agustin et al., "World Health Organization Systematic Review of Screening Tests for Preeclampsia", American College of Obstetricians and Gynecologists, Dec. 2004, pp. 1367-1391, vol. 104, No. 6.
Lane, Richard D., "A Short-Duration Polyethylene Glycol Fusion Technique for Increasing Production of Monoclonal Antibody-Secreting Hybridomas", Journal of Immunological Methods, 1985, pp. 223-228, vol. 81.
De Falco, Sandro, "The discovery of placenta growth factor and its biological activity", Experimental and Molecular Medicine, Jan. 2012, pp. 1-9, vol. 44, No. 1.
Malone, Fergal et al., "First-Trimester of Second-Trimester Screening, or Both, for Down's Syndrome", The New England Journal of Medicine, Nov. 10, 2005, pp. 2001-2011, vol. 353, No. 19.
Fischer, Christian et al., "FLT1 and its ligands VEGFB and PIGF: drug targets for anti-angiogenic therapy?", Nature, Dec. 2008, pp. 942-956, vol. 8.
Grill, Simon et al., "Potential markers of preeclampsia", Reproductive Biology and Endocrinology, Jul. 14, 2009, pp. 1-14, vol. 7, No. 70.
Hanley, James A. et al., "The Meaning and Use of the Area under a Receiver Operating Characteristic (ROC) Curve", Radiology, Apr. 1982, pp. 29-36, vol. 143.
Hultschig, Claus et al., "Recent advances of protein microarrays", Current Opinion in Chemical Biology, 2006, pp. 4-10, vol. 10.

(Continued)

*Primary Examiner* — Christine J Saoud
(74) *Attorney, Agent, or Firm* — McBee Moore & Vanik IP, LLC

(57) ABSTRACT

The present invention relates to an immunoassay method for placental growth factor 2 (PIGF-2) detection in pregnant subjects. Furthermore the invention relates to the use of said method for the diagnosis, prognosis, risk assessment and therapy control of prenatal disorders comprising the determination of the level of PIGF-2 in said pregnant subjects.

5 Claims, 2 Drawing Sheets

Specification includes a Sequence Listing.

(56) References Cited

OTHER PUBLICATIONS

Kirk-Othmer et al., "Luminescent Materials (Chemiluminescence)", Encyclopedia of Chemical Technology, 1993, pp. 518-562, vol. 15.
Levine, Richard J. et al., "Circulating Angiogenic Factors and the Risk of Preeclampsia", The New England Journal of Medicine, Feb. 12, 2004, pp. 672-683, vol. 350, No. 7.
Mathis, Gérard, "Rare Earth Cryptates and Homogeneous Fluoroimmunoassays with Human Sera", Clinical Chemistry, 1993, pp. 1953-1959, vol. 39, No. 9.
Merz, E., "First Trimester Screening—a New Algorithm for Risk Calculation of Chromosomal Anomalies Developed by FMF Germany", Ultraschall in Medizin, 2007, pp. 270-272, vol. 28.
Merz, E. et al., "Fetal Medicine Foundation Germany (FMF-D): a new approach to calculating the risk of chromosomal abnormalities with first-trimester screening data (11 + 1) to 14 + 0 weeks)", Ultrasound in Obstetrics & Gynecology, 2007, pp. 542-543, vol. 30.
Palomaki, Glenn E. et al., "Maternal serum [alpha]-fetoprotein, age, and Down syndrome risk", American Journal of Obstetrics and Gynecology, Feb. 1987, pp. 460-463, vol. 156, No. 2.
Pandya, Pranav et al., "Maternal Serum Placental Growth Factor in Prospective Screening for Aneuploidies at 8-13 Weeks' Gestation", Fetal Diagnosis and Therapy, Jan. 27, 2012, pp. 87-93, vol. 31.
Poon, Leona C. Y. et al., "Maternal serum placental growth factor (PlGF) in small for getsational age pregnancy at 11 +0 to 13+6 weeks of gestation", Prenatal Diagnosis, Nov. 10, 2008, pp. 1110-1115, vol. 28.
Schetinin, Vitaly et al., "Confident Interpretation of Bayesian Decision Tree Ensembles for Clinical Applications", IEEE Transactions on Information Technology in Biomedicine, May 2007, pp. 312-319, vol. 11, No. 3.
Schmidt, P. et al., "Unterschiedliche Berechnungsmethoden fur das Ersttrimester-Screening", Frauenarzt, 2007, pp. 1089-1092, vol. 48, No. 11.
Davies, Chris, Immunoassay Handbook, Third Edition, 2005, pp. 3-4, 14-17, 177, 185-186, 322, 499-501, 505-506.
Zaragoza, E. et al., "Maternal serum placental growth factor at 11-13 weeks in chromosomally abnormal pregnancies", Ultrasound in Obstetrics & Gynecology, 2009, pp. 382-386, vol. 33.

\* cited by examiner

METHOD DIAGNOSIS OF A PRENATAL DISORDER BY SELECTIVE DETERMINATION OF PLACENTAL GROWTH FACTOR 2

CROSS REFERENCE TO RELATED APPLICATIONS

This application is a § 371 National Stage Application of PCT/EP2014/076413, filed 3 Dec. 2014, which claims priority to EP 13195570.0, filed 3 Dec. 2013.

FIELD OF THE INVENTION

The present invention is in the field of clinical diagnostics. Particularly, the present invention relates to the determination of the level of Placental Growth Factor 2 (PlGF-2) or fragments thereof in a sample derived from a bodily fluid of a patient.

BACKGROUND OF THE INVENTION

At least 130 million women give birth every year worldwide. About 15% of them experience a pregnancy related complication or illness. For example, preeclampsia occurs in up to 5% of all pregnancies, in 10% of first pregnancies, and in 20-25% of women with a history of chronic hypertension. Hypertensive disorders in pregnancy may cause maternal and fetal morbidity, and they remain a leading source of maternal mortality.

In many countries, screening methods for determining the risk of prenatal complications and/or fetal abnormalities have become routine to aid in treating and advising pregnant women. For example, in Europe, health care providers commonly screen for chromosomal abnormalities in the fetus using biochemical markers present in maternal blood. The combination of maternal age, the serological markers pregnancy associated plasma protein A (PAPP-A) and free-beta human chorionic gonadotropin (beta-hCG) and the ultrasound marker nuchal translucency (NT) thickness has been demonstrated to function in week 11-13 with a detection rate for Down syndrome of about 82 to 90% for a false positive rate of 5% (Malone et al. 2005. *NEJM* 353 (19): 2001-2010; Bindra et al. 2002. *Ultrasound Obstet Gynecol* 20: 219-225). Such screening is helpful for identifying women who have a sufficiently high risk to justify further diagnostic testing, which can be invasive and carry a risk for the fetus. However, this screening still fails to detect a significant number of Down syndrome cases and other aneuploidy affected pregnancies and diagnoses still 5% falsely positive.

Currently no routine screens have been adopted for early detection of preeclampsia using maternal samples. The search for noninvasive biomarkers that could predict the development or assist in the detection of this life-threatening pregnancy disorder is still of utmost importance. If the development of preeclampsia could be detected earlier, better outcomes, including severity reduction and even recovery could be possible in many cases. During the pregnancy, at an early or later stage, a reliable risk assessment method for developing preeclampsia or assessment of the presence of preeclampsia would decrease the potential for negative health outcome of the pregnant woman, the baby or both.

Since many years, different biophysical and biochemical markers have been investigated, based on patho-physiological observations that have been noted in case of preeclampsia, such as placental dysfunction, a generalized inflammatory response, endothelial dysfunction and activation of the coagulation system (Grill et al. 2009. *Reproductive Biology and Endocrinology* 7:70). An imaging technique most widely used for predicting preeclampsia has been uteroplacental Doppler ultrasound. Impaired placental perfusion can be assessed by measuring flow waveform ratios or by detecting diastolic notching of the uterine arcuate vessels. However, it was shown that in both, low- and high-risk patient groups the predictive value was not sufficiently high to recommend routine screening (Conde-Agudelo et al. 2004. *Obstet Gynecol* 104: 1367-1391).

Many biological markers present in maternal samples are currently recognized as associated with preeclampsia. These potential markers include angiogenic factors (e.g. Placental growth factor (PlGF), vascular endothelial growth factor (VEGF), soluble fms-like tyrosine kinase-1 (sFlt-1)), soluble endoglin (sEng), P-selectin, cell-free fetal DNA, ADAM12, placental protein 13 (PP-13), Pentraxin 3 (PTX3) and pregnancy-associated plasma protein A (PAPP-A) (Grill et al. 2009. *Reproductive Biology and Endocrinology* 7:70). Placental growth factor (PlGF) is currently suggested for use in assessing the risk of a pregnant woman developing preeclampsia (Akolekar et al. 2008. *Ultrasound Obstet Gynecol* 32:732-739). Although PlGF has received some acceptance as a reliable marker of preeclampsia, it is desirable to have alternative and additional markers characterized by greater specificity, sensitivity and predictive power.

Thus, there exists a need for accurate screening methods for prenatal complications and/or fetal abnormalities.

Placenta growth factor (PlGF), an angiogenic glycoprotein that is homologous to vascular endothelial growth factor (VEGF), exists in humans in at least four isoforms due to alternative mRNA splicing of the PlGF primary transcript (De Falco, 2012. *Exp Mol Med* 44:1-9). These isoforms are designated PlGF-1, PlGF-2, PlGF-3 and PlGF-4. The term "PlGF" does not discriminate between the various isoforms. The main difference between the four isoforms is that PlGF-1 and 3 are non-heparin binding and can potentially affect targets in a paracrine manner, whereas PlGF-2 and 4 have additional heparin binding domains and most likely work in an autocrine way. The major isoforms are thought to be PlGF-1 and PlGF-2. PlGF-1 (SEQ ID NO:2) contains 131 amino acids (MW=monomer 14.7 kDa, dimer 29.4 kDa). PlGF-2 (SEQ ID NO:3) comprises the PlGF-1 sequence and additionally a 21 amino acid heparin binding site insertion (MW=monomer 17.3 kDa, dimer 34.6 kDa). The length of the full length PlGF-2 protein is thus 152 amino acids. PlGF-3 (SEQ ID NO:4) contains PlGF-1 and 72 amino acid insertion near the C-terminus (MW=monomer 22.8 kDa, dimer 45.6 kDa). Hence, the length of the full length PlGF-3 protein is 203 amino acids. PlGF-4 (SEQ ID NO:5) contains PlGF-3 and 21 amino acid heparin binding site insertion (MW=monomer 26.2 kDa, dimer 52.4 kDa). The length of the full length PlGF-4 is thus 224 amino acids.

PlGF is a critical regulator of angiogenesis in various physiological and pathological conditions. The exact molecular mechanisms by which different PlGF isoforms regulate blood vessel formation are still not completely understood (Fischer et al. 2008. *Nat Rev Cancer* 8:942-956). It has been reported that the angiogenic responses induced by the diverse PlGF forms are distinct (Hoffmann et al. 2013. *J Biol Chem* 288: 17976-17989). It has been demonstrated that PlGF-2 but not PlGF-1 specifically binds to heparin via a heparin-binding domain and this interaction is critical for cell migration, vessel growth and vascular sprouting.

In pregnancy, PlGF is implicated in placental development and several studies have reported that a maternal serum PlGF concentration at $11^{+0}$-b $13^{+6}$ weeks' gestation is reduced in pregnancies with fetal trisomies 21 (Down Syndrome), 18 (Edwards Syndrome) and 13 (Patau Syndrome), in those that subsequently develop preeclampsia and in those that deliver small for gestational age (SGA) neonates (Levine et al. 2004. *NEJM* 350: 672-683; Zaragoza et al. 2009. *Ultrasound Obstet Gynecol* 33: 382-386; Pandva et al. 2012. *Fetal Diagn Ther* 31:87-93; Akolekar et al. 2008. *Ultrasound Obstet Gynecol* 32:732-739; Poon et al. 2008. *Prenat Diagn* 28:1110-1115). In all these studies the major measured isoform was PlGF-1. There are no studies reporting on maternal serum concentration of PlGF-2 in normal or pathological pregnancies. Nothing is known about the absolute concentration of circulating PlGF-2 isoform in human blood and its relevance for the diagnosis of fetal aneuploidy, preeclampsia and SGA in pregnant women. WO 2010/059952 A1 reports an increased level of PlGF-2 in samples of preeclampsia patients relative to control samples.

SUMMARY

The present inventors have surprisingly found that the level of PlGF-2 is decreased in samples of subjects with a prenatal disorder. They have found that the measurement of the level of specific PlGF-2 isoform (PlGF-2) in a sample of a bodily fluid from a pregnant woman could be used for the determination whether a pregnant woman has an increased risk of developing preeclampsia, of carrying a fetus with fetal aneuploidy and/or a fetus that is small for the gestational age ("small for gestational age" (SGA)).

In the canonical PlGF precursor sequence SEQ ID NO:1 (UniProtKB/Swiss-Prot Accession no. P49763), amino acids 1 to 18 represent the signal sequence, amino acids 132 to 203 represent a domain of unknown function and in the precursor amino acids 214 to 234 represent the heparin binding domain. The amino acid sequence of PlGF-1 is represented by SEQ ID NO:2. In PlGF-2 (SEQ ID NO:3) amino acids 124 to 144 represent the heparin binding domain (SEQ ID NO:6). In PlGF-3 (SEQ ID NO:4) amino acids 114 to 185 represent a domain of unknown function (SEQ ID NO:7), referred to herein as "loop 3". In PlGF-4 (SEQ ID NO:5) amino acids 114 to 185 represent the loop 3 and amino acids 196 to 216 the heparin binding domain. In the following the amino acid sequences of the PlGF family and relatives are given; in the precursor amino acids 1 to 18 represent the signal sequence (underlined); in the precursor amino acids 214 to 234, in PlGF-2 amino acids 124 to 144, and in PlGF-4, amino acids 196 to 216 represent the heparin binding domain (italics); in the precursor amino acids 132 to 203; in PlGF-3 amino acids 114 to 185, and in PlGF-4 amino acids 114 to 185 represent a domain of unknown function (bold).

```
Precursors of PlGF (PGF) isoforms
(canonical sequence)
(SEQ ID NO: 1; Accession no. P49763):
MPVMRLFPCF LQLLAGLALP AVPPQQWALS AGNGSSEVEV

VPFQEVWGRS YCRALERLVD VVSEYPSEVE HMFSPSCVSL

LRCTGCCGDE NLHCVPVETA NVTMQLLKIR SGDRPSYVEL

TFSQHVRCEC RHSPGRQSPD MPGDFRADAP SFLPPRRSLP
```

```
-continued
MLFKMEWGCA LTGSQSAVWP SSPVPEEIPR MHPGRNGKKQ

QRKPLREKMK PERRRPKGRG KRRREKQRPT DCHLCGDAVP RR

Mature P1GF-1 (SEQ ID NO: 2):
LPAVPPQQWA LSAGNGSSEV EVVPFQEVWG RSYCRALERL

VDVVSEYPSE VEHMFSPSCV SLLRCTGCCG DENLHCVPVE

TANVTMQLLK IRSGDRPSYV ELTFSQHVRC ECRPLREKMK

PERCGDAVPR R

Mature P1GF-2 (SEQ ID NO: 3):
LPAVPPQQWA LSAGNGSSEV EVVPFQEVWG RSYCRALERL

VDVVSEYPSE VEHMFSPSCV SLLRCTGCCG DEDLHCVPVE

TANVTMQLLK IRSGDRPSYV ELTFSQHVRC ECRPLREKMK

PERRRPKGRG KRRREKQRPT DCHLCGDAVP RR

Mature P1GF-3 (SEQ ID NO: 4):
LPAVPPQQWA LSAGNGSSEV EVVPFQEVWG RSYCRALERL

VDVVSEYPSE VEHMFSPSCV SLLRCTGCCG DENLHCVPVE

TANVTMQLLK IRSGDRPSYV ELTFSQHVRC ECRHSPGRQS

PDMPGDFRAD APSFLPPRRS LPMLFRMEWG CALTGSQSAV

WPSSPVPEEI PRMHPGRNGK KQQRKPLREK MKPERCGDAV PRR

Mature P1GF-4 (SEQ ID NO: 5):
LPAVPPQQWA LSAGNGSSEV EVVPFQEVWG RSYCRALERL

VDVVSEYPSE VEHMFSPSCV SLLRCTGCCG DENLHCVPVE

TANVTMQLLK IRSGDRPSYV ELTFSQHVRC ECRHSPGRQS

PDMPGDFRAD APSFLPPRRS LPMLFRMEWG CALTGSQSAV

WPSSPVPEEI PRMHPGRNGK KQQRKPLREK MKPERRRPKG

RGKRRREKQR PTDCHLCGDA VPRR

Heparin binding domain (SEQ ID NO: 6)
RRPKGRGKRR REKQRPTDCH L

"loop 3" (SEQ ID NO: 7)
HSPGRQSPDM PGDFRADAPS FLPPRRSLPM LFRMEWGCAL

TGSQSAVWPS SPVPEEIPRM HPGRNGKKQQ RK
```

The present invention relates to a method for the diagnosis, prognosis, risk assessment, risk stratification and/or therapy control of a prenatal disorder or condition in a pregnant female subject or the unborn fetus of said subject, comprising
(i) determining the level of placental growth factor 2 (PlGF-2) in a sample from the subject,
(ii) comparing the determined level in the sample to a control level derived from subjects without a prenatal disorder or condition; wherein a decreased level in the sample from the subject as compared to the control level is indicative for the prenatal disorder or condition and/or an increased risk of the subject or fetus to acquire the prenatal disorder or condition and/or an increased risk of an aggravation of the prenatal disorder or condition.

The invention further relates to a method for diagnosing a prenatal disorder or condition in a pregnant female subject or the unborn fetus of said subject, wherein the level of placental growth factor 2 (PlGF-2) is determined in a sample from the subject to be diagnosed and wherein a level of PlGF-2 below a "multiple of the median" (MoM) of 0.90, 0.85, 0.80, 0.75, or 0.70 is indicative for the prenatal disorder or condition.

Moreover, the invention pertains to an immunoassay method for the detection of placental growth factor 2 (PlGF-2) comprising the steps of (a) contacting a sample suspected of comprising PlGF-2 with a first antibody or an antigen-binding fragment or derivative thereof specific for PlGF and a second antibody or an antigen-binding fragment or derivative thereof specific for PlGF-2 under conditions allowing for the formation of a ternary complex between PlGF-2 and the two antibodies or antigen binding fragments or derivatives thereof, and (b) detecting the binding of the two antibodies or antigen-binding fragments or derivatives thereof to PlGF-2.

The immunoassay method of the invention can be used in the context of the diagnostic method of the invention. The invention further relates to antibodies and kits for the use in the methods of the invention.

DETAILED DESCRIPTION OF A PREFERRED EMBODIMENT

Figure 1:
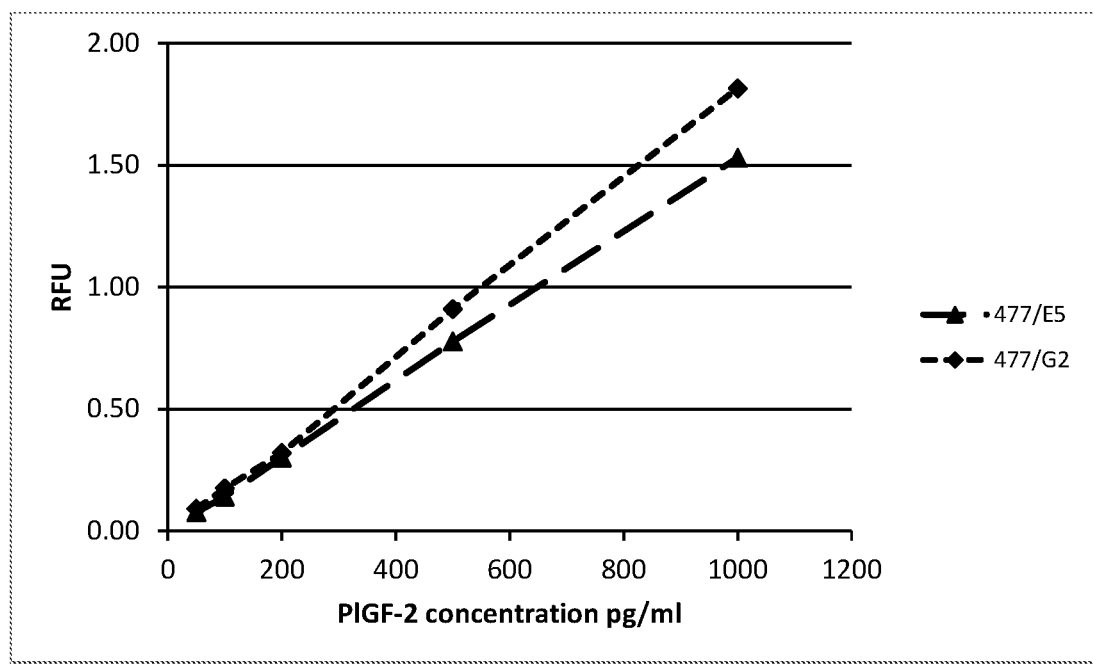
FIG. 1 shows the dose response curves for the monoclonal PlGF-2 antibodies 477/E5 and 477/G2.

The present invention provides a method for the diagnosis, prognosis, risk assessment and/or therapy control of a prenatal disorder or condition. The prenatal disorder or condition may be a maternal disorder or condition or a fetal disorder or condition. The method is based on the specific detection of the level of PlGF isoform 2 (PlGF-2) in a maternal sample, i.e. the PlGF-2 level is determined in a sample of a pregnant female subject. A PlGF-2 level that is decreased with respect to a control group is indicative for the prenatal disorder(s) or condition(s). Hence, the diagnostic method of the invention may be used for the diagnosis, prognosis, risk assessment, risk stratification and/or therapy control of a prenatal disorder or condition in the pregnant female subject or in her unborn fetus.

Hence, in one aspect the present invention relates to a method for the diagnosis, prognosis, risk assessment, risk stratification and/or therapy control of a prenatal disorder or condition in a pregnant female subject or the unborn fetus of said subject, comprising (i) determining the level of placental growth factor 2 (PlGF-2) in a sample from the subject, (ii) comparing the determined level in the sample to a control level derived from subjects without a prenatal disorder or condition; wherein a decreased level in the sample from the subject as compared to the control level is indicative for the prenatal disorder or condition and/or an increased risk of the subject or fetus to acquire the prenatal disorder or condition and/or an increased risk of an aggravation of the prenatal disorder or condition.

The invention further relates to a method for diagnosing a prenatal disorder or condition in a pregnant female subject or the unborn fetus of said subject, wherein the level of placental growth factor 2 (PlGF-2) is determined in a sample from the subject to be diagnosed and wherein a level of PlGF-2 below a "multiple of the median" (MoM) of 0.90, 0.85, 0.80, 0.75, or 0.70 of the control group is indicative for the prenatal disorder or condition. A multiple of the median (MoM) is a measure of how far an individual test result deviates from the median oft eh control group. MoM is commonly used to report the results of medical screening tests, particularly where the results of the individual tests are highly variable. Concentrations of prenatal screening analytes change constantly throughout pregnancy. For example, AFP concentrations in maternal serum increase by about 15% per week during the most favorable time for detecting open neural tube defects (15-20$^{th}$ week of gestation). Converting these values to a gestational age-specific median value (MoM) normalizes for this gestational age effect. A laboratory therefore may first obtain measures on sera obtained routinely from e.g. 300 to 500 women. Measurements are initially expressed in mass units (e.g. ng/ml) or interational units (e.g. IU/ml). Weighted log-linear regression analysis is used to calculate an equation to determine median levels for the analyte in question for each gestational week. Each women's measurement is then divided by the median value for the appropriate gestational age resulting in a multiple of the median (MoM). The overall median value in a population of women is, by definition, 1.00 MoM. A "multiple of the median" indicates the factor applied to a median value, e.g. 0.90 means 90% of the median value. Preferred MoM values are 0.85, 0.80 or 0.75, more preferred are 0.80 and 0.75 and most preferred is 0.75. Suitable threshold values can, for example be derived from Table 2 below. In the following exemplary threshold values will be discussed. However, depending on the desired specificity and/or sensitivity or the control group, other threshold values may be used. For example, a value below 122.3 pg/ml (corresponding to a MoM of 0.83) may be indicative for preeclampsia. A value below 128.7 pg/ml (corresponding to a MoM of 0.75) may be indicative for small for gestational age. Suitable threshold values for trisomy 13, trisomy 18 and trisomy 21 are e.g. 125 pg/ml (corresponding to a MoM of 0.75), 113 pg/ml (corresponding to a MoM of 0.81) and 99.6 pg/ml (corresponding to a MoM of 0.76), respectively.

Alternatively, newly developed "degrees of extremeness" (DoE) instead of MoM can be used for risk calculation with blood-derived markers (Merz 2007. *Ultraschall in Med* 28: 270-272; Schmidt et al. 2007. *Frauenarzt* 48: 1089-1092). The DoE is a ratio of the distance between the median value and actual value and the distance between the median value and 5$^{th}$ percentile (when the measured value is below the median) or the distance between the median and the 95$^{th}$ percentile (when the measured value is above the median) (Merz 2007. *Ultraschall in Med* 28: 270-272; Merz et al. 2007. *Ultrasound Obstet Gynecol* 30: 542-543). Under this assumption, a DoE is 0 at the median value, 1.0 at the 95$^{th}$ percentile, and −1.0 at the 5$^{th}$ percentile. Additionally, the Bayesian theorem (Schetinin et al. 2007. *IEEE Trans Inf Technol Biomed* 11: 312-319) can be used instead of the mathematical concept of sequential likelihood ratios of Palomaki and Haddow (Palomaki and Haddow 1987. *Am J Obstet Gynecol* 156: 460-463).

The prenatal disorder or condition may be a disorder or condition of the pregnant female subject or the unborn fetus of the subject. For example, the prenatal disorder or condition may be preeclampsia in the pregnant female subject. The prenatal disorder or condition may also relate to adverse pregnancy outcomes such as the risk of the female subject to deliver a child being "small for gestational age" or having an abnormality such as aneuploidy. The prenatal disorder or condition of the fetus may therefore for example be "small for gestational age" or aneuploidy.

In another aspect the present invention relates to an immunoassay method for the detection of PlGF-2 that can be used in the context of the diagnostic method of the invention. The immunoassay method is based on the detection of PlGF-2 using an antibody, preferably a monoclonal antibody, that is specific for PlGF-2, i.e. this antibody preferably does not cross-react with other antigens, particularly the other isoforms of PlGF-2. In the immunoassay, a combination of two antibodies may be used, e.g. in a sandwich format (see below), of which at least one antibody is specific for PlGF-2: For instance, a first antibody is specific for PlGF (not necessarily for the isoform 2 but in any case able to bind to PlGF-2) and the second antibody is specific for PlGF-2. Hence, the present invention pertains to an immunoassay method for the detection of placental growth factor 2 (PlGF-2) comprising the steps of
(a) contacting a sample suspected of comprising PlGF-2 with a first antibody or an antigen-binding fragment or derivative thereof specific for PlGF and a second antibody or an antigen-binding fragment or derivative thereof specific for PlGF-2 under conditions allowing for the formation of a ternary complex between PlGF-2 and the two antibodies or antigen-binding fragments or derivatives thereof, and
(b) detecting the binding of the two antibodies or antigen-binding fragments or derivatives thereof to PlGF-2.

In the following the term "antibody" also comprises antigen-binding fragments or derivatives unless otherwise stated. The first antibody can be any antibody specific for PlGF as long as it detects PlGF-2. Such antibodies are commercially available. For example, the first antibody may be a polyclonal antibody against human PlGF. Such an antibody can be purchased e.g. from R&D Systems Europe Ltd. (Ref. No: AF-264-PB).

In the immunoassay method according to the invention said second antibody may be specific for an epitope in the sequence of PlGF-2 (SEQ ID NO:3), preferably in the heparin-binding domain (SEQ ID NO:6). However, it is preferred that the second antibody is directed to a conformational epitope of PlGF-2 that is not present in the other PlGF isoforms. The second antibody is preferably a monoclonal antibody.

As will be discussed herein below in more detail the (first and/or second) antibodies or antigen-binding fragments or derivatives thereof of the immunoassay method as described herein may for instance be polyclonal antibodies, monoclonal antibodies or genetically engineered monoclonal antibodies.

Preferably herein, said first and second antibodies or antigen-binding fragments or derivatives thereof are specific for different conformational and non-overlapping epitopes of PlGF-2.

The first antibody or antigen-binding fragment or derivative thereof may for example be specific for an epitope comprised within the sequence of SEQ ID NO:1.

The second antibody or antigen-binding fragment or derivative thereof may, for example, be produced by a hybridoma cell line selected from cell line 477/G2 deposited on Nov. 21, 2013 at the Leibniz-Institut DSMZ-Deutsche Sammlung von Mikroorganismen and Zellkulturen GmbH (DSMZ; Inhoffenstr. 7B, Braunschweig, Germany), as DSM ACC3222 and cell line 477/E5 deposited on Nov. 21, 2013 at the DSMZ as DSM ACC3221, preferably herein the second antibody is produced by hybridoma cell line 477/G2 deposited as DSM ACC3222.

Preferably herein, the first antibody is a polyclonal anti-PlGF antibody, e.g. the commercially available antibody provided by R&D Systems Europe Ltd. Abingdon UK under Ref. No.: AF-264-PB. In a specific embodiment the first antibody is a polyclonal anti-PlGF antibody, e.g. the commercially available antibody provided by R&D Systems Europe Ltd. Abingdon UK under Ref. No.: AF-264-PB and the second antibody is the antibody produced by hybridoma cell line 477/G2 deposited as DSM ACC3222.

The binding of the antibodies to PlGF-2 takes place under suitable conditions (i.e. allowing for immunoreactions, i.e. binding of the antibodies to PlGF-2 on formation of immune complexes). Such conditions are known to the skilled person and standard formats of immunoassays e.g. as described below can be used. Such conditions will preferably be under physiologic temperature, pH and ionic strength and can take place in media such as, for example, phosphate buffered saline (PBS).

The preferred detection methods comprise immunoassays in various formats such as for instance radioimmunoassay (RIA), chemiluminescence- and fluorescence-immunoassays, enzyme immunoassay (EIA), Enzyme-linked immunoassays (ELISA), Luminex-based bead arrays, protein microarray assays, rapid test formats such as for instance immunochromatographic strip tests, and Selected/Multiple reaction monitoring (SRM/MRM).

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134, incorporated herein by reference).

In a particularly preferred embodiment, the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

Even more preferred, said labelling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4', 7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like. In the context of the present invention, chemiluminescence based assays comprise the use of dyes, based on the physical principles described for chemiluminescent materials in Kirk-Othmer, *Encyclopedia of chemical technology*, 4$^{th}$ ed., executive editor, J. I. Kroschwitz; editor, M Howe-Grant, John Wiley & Sons, 1993, vol. 15, p. 518-562, incorporated herein by reference, including citations on pages 551-562. Preferred chemiluminescent dyes are acridiniumesters. PlGF-2 may for example be detected using fully automated sandwich immunoassay systems on the B.R.A.H.M.S KRYPTOR compact PLUS instrument (Thermo Scientific B.R.A.H.M.S GmbH, Hennigsdorf/Berlin, Germany). This random access analyzer employs the sensitive Time Resolved Amplified Cryptate Emmission (TRACE) technology, based on a non-radioactive-transfer between two fluorophores.

In specific embodiments of the invention one of the antibodies (e.g. the first antibody) is labeled and the other antibody (e.g. the second antibody) is bound to a solid phase or can be bound selectively to a solid phase. However, as mentioned above, it is preferred in the context of methods of the invention that the first and the second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to the PlGF-2 to be detected, a measurable signal which permits detection of the resulting sandwich complexes in the measuring solution is generated.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ M$^{-1}$.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive is the assay. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having a prenatal discorder or condition) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disorder or condition ("diseased group"). In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

The term "antibody" generally comprises monoclonal and polyclonal antibodies and binding fragments thereof, in particular Fc-fragments as well as so called "single-chain-antibodies" (Bird R. E. et al (1988) *Science* 242:423-6), chimeric, humanized, in particular CDR-grafted antibodies, and dia or tetrabodies (Holliger P. et al (1993) *Proc. Natl. Acad. Sci. U.S.A.* 90:6444-8). Also comprised are immunoglobulin like proteins that are selected through techniques including, for example, phage display to specifically bind to the molecule of interest contained in a sample. In this context the term "specific binding" refers to antibodies raised against the molecule of interest or a fragment thereof. An antibody is considered to be specific, if its affinity towards the molecule of interest or the aforementioned fragment thereof is at least preferably 50-fold higher, more preferably 100-fold higher, most preferably at least 1000-fold higher than towards other molecules comprised in a sample containing the molecule of interest. It is well known in the art how to make antibodies and to select antibodies with a given specificity. As stated herein above, monoclonal antibodies are preferred.

The present invention also relates to a monoclonal antibody which is produced by a hybridoma cell line selected from cell line 477/G2 deposited as DSM ACC3222 and cell line 477/E5 deposited as DSM ACC3221. The invention also pertains to an antibody that binds to the same epitope as the antibody produced by a hybridoma cell line selected from cell line 477/G2 deposited as DSM ACC3222 and cell line 477/E5 deposited as DSM ACC3221.

The invention further relates to a kit for the detection of PlGF-2 comprising
(i) a first antibody or antigen-binding fragment or derivative thereof which is specific for PlGF; and
(ii) a second antibody or antigen-binding fragment or derivative thereof which is specific for PlGF-2.

For example, (i) the first antibody or antigen-binding fragment or derivative thereof is specific for an epitope comprised within the sequence of SEQ ID NO: 1; and/or (ii) the second antibody or antigen-binding fragment or derivative thereof is specific for a structural epitope of PlGF-2. Preferably, the first antibody of the kit is a polyclonal anti-PlGF antibody, e.g. the commercially available antibody provided by R&D Systems Europe Ltd. Abingdon UK under Ref. No.: AF-264-PB. In a specific embodiment of the kit the first antibody is a polyclonal anti-PlGF antibody, e.g. the commercially available antibody provided by R&D Systems Europe Ltd. Abingdon UK under Ref. No.: AF-264-PB and the second antibody is the antibody produced by hybridoma cell line 477/G2 deposited as DSM ACC3222.

In one embodiment of the kit, the second antibody is a monoclonal antibody which is produced by a hybridoma cell line selected from cell line 477/G2 deposited as DSM ACC3222 and cell line 477/E5 deposited as DSM ACC3221, preferably the monoclonal antibody which is produced by a hybridoma cell line selected from cell line 477/G2 deposited as DSM ACC3222.

The present invention also provides a hybridoma cell line selected from cell line 477/G2 deposited as DSM ACC3222 and cell line 477/E5 deposited as DSM ACC3221.

The invention e.g. further relates to the use of a kit according to the present invention in a sandwich immunoassay format for the detection and/or quantification of PlGF-2 or a fragment thereof in a biological sample from a bodily fluid. Such a fragment at least comprises a sequence spanning the two epitopes against which the two antibodies are directed, e.g. the kit can be used for the detection and/or quantification of total PlGF-2.

The term "sample" is preferably a biological sample. "Sample" as used herein may, e.g., refer to a sample of bodily fluid or tissue obtained for the purpose of diagnosis, prognosis, or evaluation of a subject of interest, such as a patient. A "patient" or "subject" for the purposes of the present invention includes both humans and other animals, particularly mammals, and other organisms. Thus, the methods are applicable to both human diagnostics and veterinary applications. In a preferred embodiment the patient is a mammal, and in the most preferred embodiment the patient or subject is a human.

Preferably herein, the sample is a sample of a bodily fluid or a tissue of the pregnant female subject. A bodily fluid sample is preferred. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components. Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, more preferably a serum sample or a plasma sample. Serum samples are the most preferred samples in the context of the present invention.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

The method of the invention further relates to the determination of the level of PlGF-2 in a sample for diagnosis or prognosis or risk assessment or screening for medical conditions.

In a further embodiment of the invention the method according to the invention may be used to detect total PlGF-2 for diagnosis or prognosis or risk assessment or screening for prenatal disorders comprising the steps of
(i) providing a sample of a bodily fluid of a subject,
(ii) determining the amount of PlGF-2 in said subjects sample,
(iii) comparing the amount of PlGF-2 with a reference sample, wherein a decrease from the reference sample indicates the presence of a prenatal disorder.

The immunoassay, antibody or kit of the invention may therefore be used for the diagnosis, prognosis, risk assessment, risk stratification and/or for therapy control of a disorder or condition in a subject.

In the context of the present invention the disorder or condition is preferably a prenatal disorder or condition in a pregnant female subject or in a fetus. In the context of the present invention, the prenatal disorder or condition in the pregnant female subject is preferably selected from preeclampsia or the risk of delivery of a child with an aneuploidy or the risk of delivery of a small for gestational age neonate.

In the context of the present invention, said subject may be in the first, second or third trimester of pregnancy. Preferably, the subject is in the first trimester of the pregnancy. However, the subject may also be in the second trimester. The subject may also be in the third trimester. In particular in the case of preeclampsy or small for gestational age, the subject may be in the $1^{st}$, $2^{nd}$ or $3^{rd}$ trimester of pregnancy, preferably the $1^{st}$ trimester.

In the context of the diagnostic and prognostic methods of the invention, further decisive parameters may be determined in addition to the PlGF-2 level. For example information relating to the age, weight and/or body mass index (BMI) may additionally be used for diagnosing. Further parameters include the presence or former presence of other diseases or conditions in the subject. Moreover, other relevant biomarkers may be determined in the subject, e.g. in the same sample as used for the method of the invention. Hence, in some embodiments at least one further parameter relevant for diagnosis is determined in the sample. Therefore, PlGF-2 may be part of a marker panel used in the diagnostic or prognostic methods of the invention. For example, when the disorder or condition is preeclampsia, the further parameter may be one or more selected from the group consisting of PAPP-A, ultrasound markers (Pulsatile-Index, diastolic notching), Mean Arterial Pressure, PlGF, sFlt, maternal history, soluble Endoglin (sEng), inhibin A, activin A, vascular endothelial growth factor (VEGF), human chorionic gonadotrophin (hCG) and cell free fetal DNA. For example, when the disorder or condition is aneuploidy, the further parameter may be one or more selected from the group consisting of PAPP-A, free-beta hCG, nuchal translucency, maternal age, AFP, PlGF, fetal nasal bone, biparietal diameter/nasal bone ratio, hCG, inhibin A, unconjugated estriol 3 (uE3), and cell free fetal DNA. For example, when the disorder or condition is "small for gestational age", the further parameter may be one or more selected from the group consisting of PAPP-A, maternal history, PlGF, sFlt, AFP, free-beta hCG, hCG, inhibin-A, activin A, sEng, symphysis-fundal height (SFH), fetal biometry (femur length (FL), head circumference (HC), biparietal diameter (BPD), abdominal circumference (AC)) and ultrasound markers (Pulsatile-Index, Umbilical artery Doppler, Middle cerebral artery Doppler, Ductus venosus Doppler). For differential diagnosis, in addition to the level of PlGF-2 other markers and information may be used.

The term "biomarker" (biological marker) relates to measurable and quantifiable biological parameters (e.g., specific enzyme concentration, specific hormone concentration, specific gene phenotype distribution in a population, presence of biological substances) which serve as indices for health- and physiology-related assessments, such as disease risk, psychiatric disorders, environmental exposure and its effects, disease diagnosis, metabolic processes, substance abuse, pregnancy, cell line development, epidemiologic studies, etc. Furthermore, a biomarker is defined as a characteristic that is objectively measured and evaluated as an indicator of normal biological processes, pathogenic processes, or pharmacologic responses to a therapeutic intervention. A biomarker may be measured on a biosample (as a blood, urine, or tissue test), it may be a recording obtained from a person (blood pressure, ECG, or Holter), or it may be an imaging test (Uteroplacental Doppler ultrasound, or nuchal translucency (Conde-Agudelo et al. 2004. *Obstet Gynecol* 104: 1367-1391; Bindra et al. 2002. *Ultrasound Obstet Gynecol* 20: 219-225)). Biomarkers can indicate a variety of health or disease characteristics, including the level or type of exposure to an environmental factor, genetic susceptibility, genetic responses to exposures, biomarkers of subclinical or clinical disease, or indicators of response to therapy. Thus, a simplistic way to think of biomarkers is as indicators of disease trait (risk factor or risk biomarker), disease state (preclinical or clinical), or disease rate (progression). Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). Biomarkers may also serve as surrogate end points. A surrogate end point is one that can be used as an outcome in clinical trials to evaluate safety and effectiveness of therapies in lieu of measurement of the true outcome of interest. The underlying principle is that alterations in the surrogate end point track closely with changes in the outcome of interest. Surrogate end points have the advantage that they may be gathered in a shorter time frame and with less expense than end points such as morbidity and mortality, which require large clinical trials for evaluation. Additional values of surrogate end points include the fact that they are closer to the exposure/intervention of interest and may be easier to relate causally than more distant clinical events. An important disadvantage of surrogate end points is that if clinical outcome of interest is influenced by numerous factors (in addition to the surrogate end point), residual confounding may reduce the validity of the surrogate end point. It has been suggested that the validity of a surrogate end point is greater if it can explain at least 50% of the effect of an exposure or intervention on the outcome of interest. For instance, a biomarker may be a protein, peptide or a nucleic acid molecule.

Within the scope of the invention prenatal disorders preferably relate to preeclampsia, small for gestational age and aneuploidies including trisomy 13, trisomy 18 and trisomy 21.

In one embodiment of the invention the measurement of total PlGF-2 is carried out within the first trimester (1st to 13th week of pregnancy), second trimester (14th to 26th week of pregnancy) or third trimester (27th to 40th week of pregnancy).

Within the scope of the invention PlGF-2 is understood to mean human PlGF-2 according to SEQ ID NO:3. These polypeptides according to the invention may also have posttranslational modifications such as glycolization, lip(o)idization, or derivatization.

Within the scope of the invention total PlGF-2 is understood to mean free PlGF-2 and PlGF-2 bound to multimeric complexes, which can comprise for example the homodimeric PlGF-2 complex and the heterodimeric PlGF-2/VEGF-A, complex.

In a further embodiment of the invention the prognosis or risk stratification is related to an early onset (between 20 to 34 weeks of gestation) or a late onset (after 34 weeks of gestation) of preeclampsia.

In another embodiment of the invention further markers are additionally determined selected from the group sFlt-1, PlGF, VEGF, PP-13, ADAM12, P-Selectin, cell-free fetal DNA, PTX3, PAPP-A, visfatin, inhibin A, activin A, human chorionic gonadotrophin (hCG), beta-hCG, alpha-fetoprotein (AFP), metalloproteinase-9 (MMP-9), ultrasound markers (uterine artery pulsatility index and/or diastolic notching) as well as blood pressure.

In a preferred embodiment of the invention said further markers are selected from the group comprising sFlt-1, PlGF, PAPP-A, uterine artery pulsatility index and blood pressure.

The term "subject" as used herein refers to a living human or non-human female organism. Preferably herein the subject is a human subject that is pregnant within the first to third trimester, preferably in the first or second trimester and more preferably within the first trimester of pregnancy. For example, the subject is in week 11-13 of gestation. A "fetus" herein refers to a developing mammal after the embryonic stage and before birth. In humans, the fetal stage commences at the beginning of the ninth week of gestation.

The term "sample" as used herein refers to a sample as described above.

The term "reference sample" relates to a sample obtained from a subject or group of subjects who do not have a disease or disorder, and who do not develop the disease or disorder. Said subject or group of subjects represent the same gender and species as the subject being tested. The "control level" is derived from one or more "reference sample" and is preferably derived from subjects without a prenatal disorder or condition. It is preferred herein, that the "control group" is from the same trimester of pregnancy as the subject or even from the same gestational age (e.g. in terms of weeks of gestation). E.g. when the subject is in week 11-13 of gestation the control group may also be from week 11-13 of gestation.

"Diagnosis" in the context of the present invention relates to the recognition and (early) detection of a disease or clinical condition in a subject and may also comprise differential diagnosis. Also the assessment of the severity of a disease or clinical condition may in certain embodiments be encompassed by the term "diagnosis".

"Prognosis" relates to the prediction of an outcome or a specific risk for a subject suffering from a particular disease or clinical condition. This may include an estimation of the chance of recovery or the chance of an adverse outcome for said subject.

In the present invention, the term "risk stratification" relates to the grouping of subjects into different risk groups according to their further prognosis. Risk stratification also relates to stratification for applying preventive and/or therapeutic measures.

The term therapy control in the context of the present invention refers to the monitoring and/or adjustment of a therapeutic treatment of said patient.

The term "screening" in the context of the present invention refers to a process of surveying a population, using a specific marker or markers and defined screening cut-off levels, to identify the individuals in the population at higher risk for a particular disorder. Screening is applicable to a population; diagnosis is applied at the individual patient level.

The term "preeclampsia" includes a hypertensive, multi-system disorder of pregnant women, characterized by hypertension and proteinuria. The most common symptoms of preeclampsia are high blood pressure, increased protein in the urine, and swelling or edema of hands and face. In certain embodiments of the invention, preeclampsia is defined as hypertension (systolic and diastolic blood pressure of ≥140 and 90 mm Hg, respectively) and proteinuria (protein excretion of ≥300 mg in a 24 h urine collection, or a dipstick of ≥2+).

Aneuploidy is an abnormal number of chromosomes, and is a type of chromosome abnormality. An extra or missing chromosome is a common cause of genetic disorders (birth defects). Aneuploidy occurs during cell division when the chromosomes do not separate properly between the two cells. Aneuploidy includes for example fetal trisomies 21 (Down Syndrome), 18 (Edwards Syndrome) and 13 (Patau Syndrome).

Small for gestational age refers to a fetus with growth restriction that has not reached its determined potential size. Fetal weight is below the 10th percentile for gestational age.

The following examples and figures are used for a more detailed explanation of the invention, but do not limit the invention to said examples and figures.

All patent and non-patent references cited herein are hereby incorporated by reference in their entirety.

EXAMPLES

Example 1

Generation of Antibodies

Polyclonal Antibody

Polyclonal antibody directed against human PlGF was commercially purchased from (R&D Systems Europe Ltd. Abingdon UK; Ref No: AF-264-PB).

Development of Monoclonal Antibodies

Monoclonal antibodies against PlGF-2 were generated by standard procedures (Harlow E, Lane D. *Antibodies—A Laboratory Manual*. Cold Spring Harbor: Cold Spring Harbor Laboratory, 1988; Lane 1985. *Journal of Immunology Methods* 81: 223-228). For the generation of anti-human PLGF-2 antibodies, 8-week-old female BALB/c mice were immunized with 50 μg human recombinant PlGF-2 (R&D Systems Europe Ltd. Abingdon UK) dissolved in 11 mmol/L sodium phosphate buffer (pH 7.2) containing 140 mmol/L NaCl. Subsequent booster injections of immunogen were administrated in 4-week intervals. The fusion was done with SP2/0 mouse myeloma cells (SP2/0-Ag 14) 3 months after initial immunization. The clones 477/G2 and 477/E5 were screened by ELISA with immobilized recombinant human PlGF-2. The antibodies were purified by protein A Fast Flow affinity chromatography (GE Healthcare Life Sciences) according to the manufacturer's instructions.

The selection of the monoclonal antibody was based on the signal obtained for the recognition of the recombinant PlGF-2 (SEQ ID NO:3). The two dose response curves are shown in FIG. 1. The best signal was obtained using the clone 477/G2.

Labelling of Antibodies

In the assay, polyclonal anti-human PlGF antibody (R&D Systems Europe Ltd. Abingdon UK) and monoclonal anti-human PlGF-2 antibody were coupled to Lumi4®-Tb (Lumiphore, Inc., Richmond, Canada) and to cyanine 5.5 (GE Healthcare UK Limited), respectively. The coupling reactions were performed according to the manufacturer's prescribed coupling protocols.

Example 2

Development of a PlGF-2 Assay Using Monoclonal and Polyclonal Antibodies

A homogenous sandwich fluoroimmunoassay using Time Resolved Amplified Cryptate Emission (TRACE) technology (Mathis, 1993. *Clin Chem* 39(9): 1953-9) was developed for the detection of PlGF-2.

The stock Lumi4®-Tb-conjugated antibody and cyanine 5.5-conjugated antibody solution were diluted at 0.125 μg/mL and 5 μg/mL with assay buffer (100 mmol/L sodium phosphate pH 7, 0.375% bovine serum albumin free protease, 0.25 mg/mL mouse IgG, 0.25 mg/mL bovine IgG, 0.25 mg/mL goat IgG), respectively, prior to use. The recombinant human PlGF-2 was diluted in defibrinated normal human plasma heat treated to give PlGF-2 standards. The immunoassay was performed by incubating 70 μL of samples/calibrators, 40 μL of cyanine 5.5-conjugated antibody solution and 40 μL of Lumi4®-Tb-conjugated antibody solution at 37° C. on B.R.A.H.M.S KRYPTOR compact PLUS instrument (Thermo Scientific B.R.A.H.M.S GmbH, Hennigsdorf/Berlin, Germany), according to the manufacturer's instructions. The reaction time of the assay was 29 min. The specific fluorescence (RFU) was measured by simultaneous dual wavelength measurement at 707 and 620 nm using a B.R.A.H.M.S KRYPTOR compact PLUS instrument.

Example 3

Dose Response Curve of the Assay with Clone 477/G2

Figure 2:
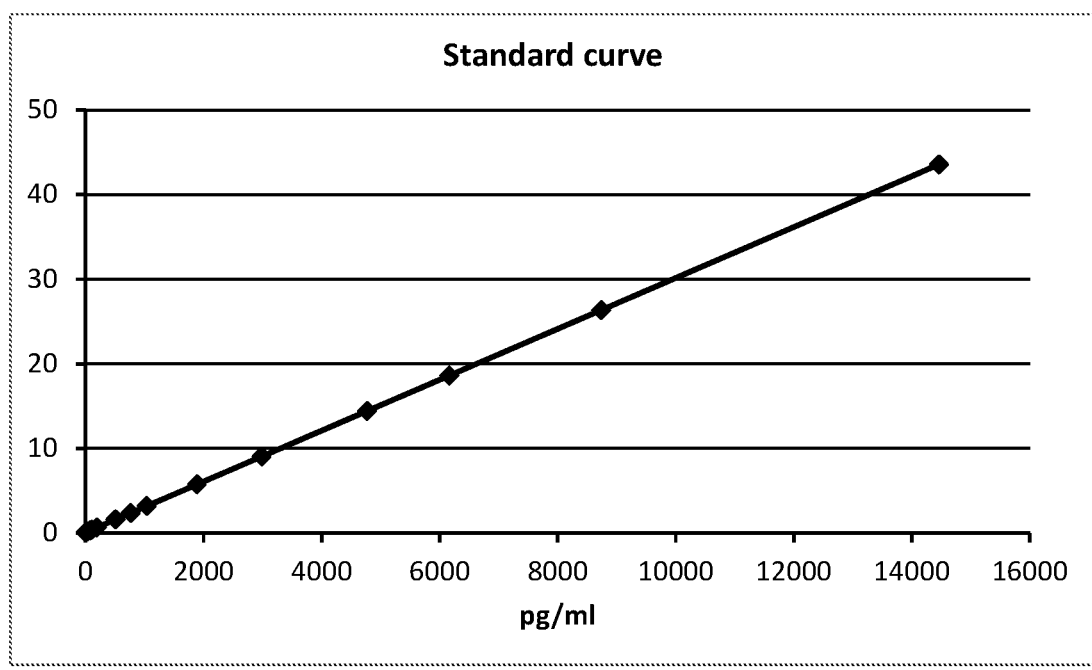
FIG. 2 shows the dose response curve for the PlGF-2 homogenous sandwich fluoroimmunoassay using Time Resolved Amplified Cryptate Emission (TRACE) technology of examples 2 and 3.

A dose response curve could be created by using the recombinant PlGF-2 (SEQ ID NO:3) as standard material in the monoclonal immunoassay as described above. A typical dose response curve is shown in FIG. 2.

Example 4

Specificity of PlGF-2 Isoform Recognition by the Assay

Figure 3:
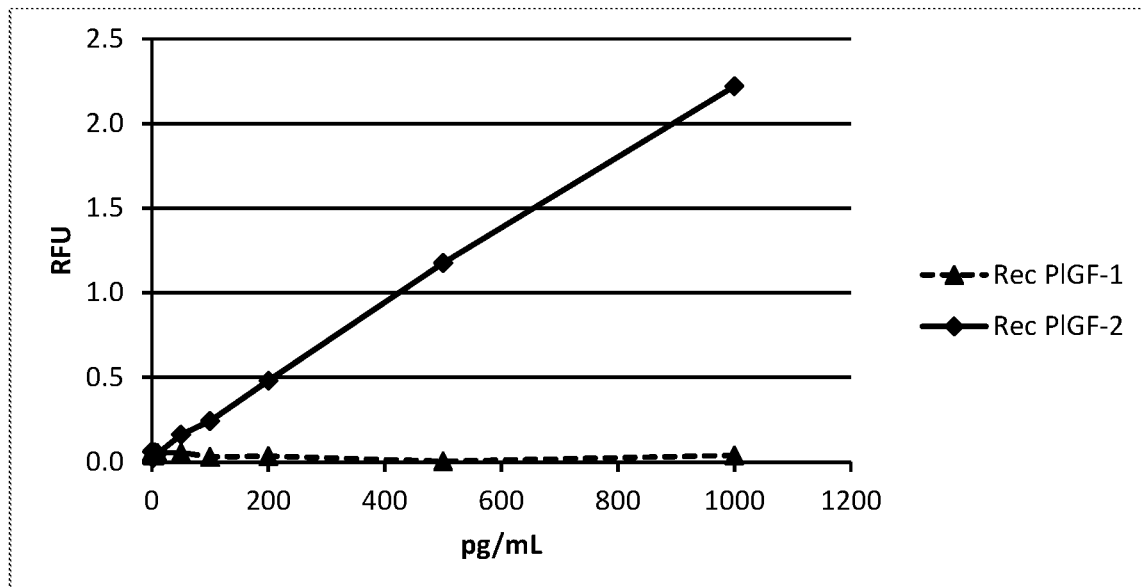
FIG. 3: Dose response curves for PlGF-1 and PlGF-2 show that the specific assay for PlGF-2 has no cross-reactivity for the PlGF-1 isoform (example 4).

Commercial PlGF-1 and PlGF-2 standards were measured using the specific PlGF-2 assay. FIG. 3 shows that the specific assay for PlGF-2 has no cross-reactivity with PlGF-1 isoform, thus this method detects only the specific PlGF-2 isoform.

Example 5

Recognition of a Conformational Epitope on PlGF-2 Isoform

Figure 4:
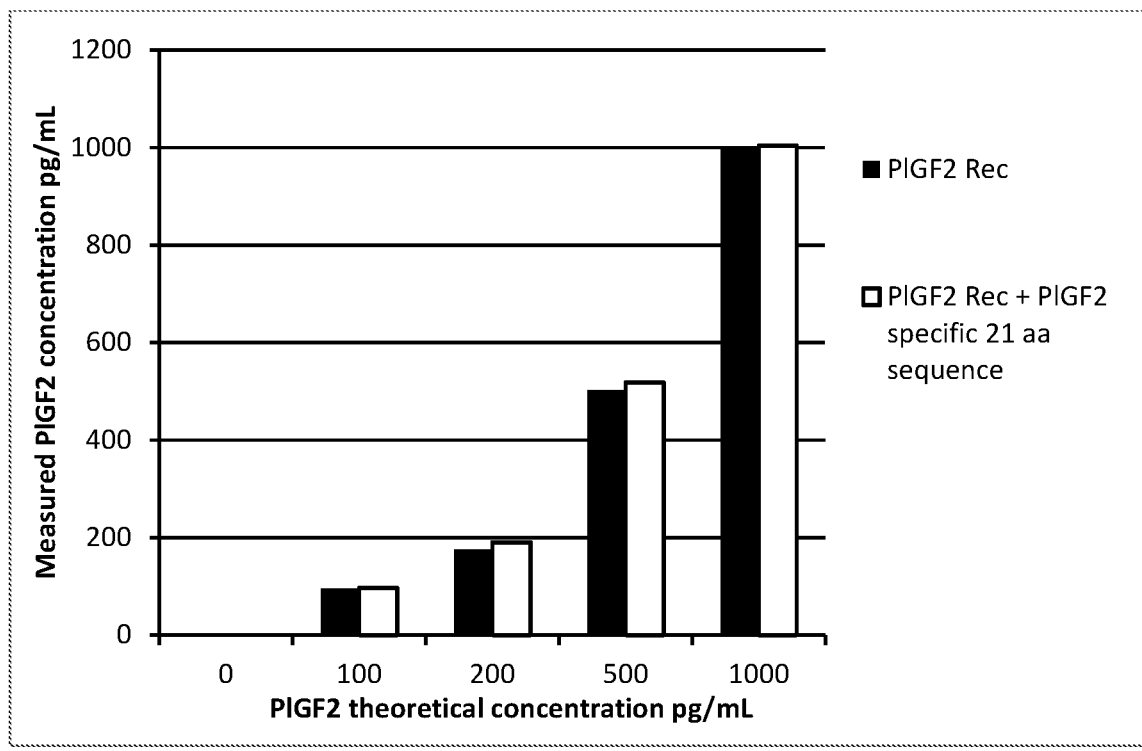
FIG. 4: Determination of PlGF-2 concentration in the presence and absence of a 21-aa peptide corresponding to the heparin-binding site. There was no inhibition of the signal when the specific heparin-binding domain peptide was added in the assay, therefore the linear 21 as peptide corresponding to the SEQ ID NO:6 was not recognized by the monoclonal antibody 477/G2.

Recombinant PlGF-2 was assayed using the specific PlGF-2 assay. Samples were prepared to contain 10 μg/mL of 21 aa peptide specific to heparin binding domain of PlGF-2 (SEQ ID NO:6). High concentration of 21 aa peptide has been used ($1 \times 10^6$ times higher compared to recombinant PlGF-2) in order to inhibit the recognition of the recombinant PlGF-2 by the assay. There was no inhibition of the signal when the specific heparin-binding domain peptide was added in the assay (FIG. 4), therefore the linear 21aa peptide corresponding to the SEQ ID NO: 6 was not recognized by the monoclonal antibody 477/G2. This antibody recognized a conformational epitope on PlGF-2 isoform.

Example 6

PlGF-2 in Prenatal Disorders

Study Population

To determine whether PlGF-2 is a useful marker for pathological pregnancies, the homogenous sandwich fluoroimmunoassay for PlGF-2 described above was used to evaluate PlGF-2 in serum samples from 295 women who underwent normal pregnancies, 15 pregnancies affected by trisomy 21, 10 trisomy 18, 10 trisomy 13, 30 pregnancies that subsequently developed PE requiring delivery before 34 weeks and 30 cases that delivered small for gestational age (SGA) neonates. The specific PlGF-2 assay was calibrated with recombinant human PlGF-2.

Samples were taken at the routine first trimester hospital visit. All pregnant women signed a consent form approved by King's College Hospital Ethics Committee.

Measurements

PlGF-2 was detected using fully automated sandwich immunoassay systems on the B.R.A.H.M.S KRYPTOR compact PLUS instrument (Thermo Scientific B.R.A.H.M.S GmbH, Hennigsdorf/Berlin, Germany). This random access analyzer employs the sensitive Time Resolved Amplified Cryptate Emmission (TRACE) technology, based on a non-radioactive-transfer between two fluorophores. The automated assay for the detection of PlGF-2 is essentially based on the sandwich fluorescence assay using a commercially available polyclonal antibody (R&D Systems Europe Ltd. Abingdon UK; Ref No: AF-264-PB) and a novel monoclonal antibody which is specifically binding to PlGF-2 and described above. The specific PlGF-2 assay was calibrated with recombinant human PlGF-2. The B.R.A.H.M.S PlGF-2 KRYPTOR assay had a measuring range of 15 to 14 461 pg/mL (FIG. 2). The variation of PlGF-2 assay was determined for the control samples in 26 runs with 2 replicates. The calibration curve of the first run was used as a reference curve during 7-day period. The limit of detection was 15 pg/mL and the limit of quantitation (functional sensitivity) was <42 pg/mL. The intra-assay and inter-assay variations were 8.8% and 9.4%, respectively at a PlGF-2 concentration of 100 pg/mL, 2.3% and 2.9% at 505 pg/mL, 1.3% and 2.4% at 1018 pg/mL.

For determining the risk of chromosomal abnormality in the fetus the following parameters were measured in samples from pregnant women taken during the first trimester: i) PAPP-A, free beta hCG, ii) PAPP-A, free beta hCG, PlGF, iii) PAPP-A, free beta hCG, PlGF, PlGF-2. The detection rate and false positive rate were determined using an algorithm combining these biomarkers.

For risk assessment analysis of the development of preeclampsia in pregnant women the following parameters were measured in samples from said subjects taken during the first trimester: i) PAPP-A, PI, MAP, ii) PAPP-A, PI, MAP and PlGF iii) PAPP-A, PI, MAP, PlGF and PlGF-2. The detection rate and false positive rate were determined using an algorithm combining these biomarkers.

Statistical Analysis

Mathematical algorithms to determine risk of fetal aneuploidy are calculated by determining the medians for the normal population and the respective fetal aneuploidy population. PAPP-A, free beta hCG, PlGF and PlGF-2 are expressed in Multiples of the median (MoMs) in order to standardized the findings. A prior risk (expressed as odds) is derived from the maternal age-specific prevalence, and is multiplied by an likelihood ratio (LR) from the log Gaussian distributions of biochemical markers in affected and unaffected pregnancies. For combinations of PAPP-A, free beta hCG, PlGF and PlGF-2, correlation coefficients between log MoM values in affected and unaffected pregnancies are determined.

The statistical process for carrying out the risk estimate is calculated by determining the medians for the unaffected pregnancies and the preeclamptic pregnancies. For each biochemical and biophysical marker a MoM is calculated. Multivariate Gaussian analysis is then performed to determine likelihood ratios. For preeclampsia risk determination, the prior risk was based on general population risk. Mann-Whitney U test was applied to determine the significance of differences in the median MoM values in each outcome group to that in the controls.

Results

The patients's characteristics are shown in Table 1. The median MoM of PlGF-2 compared to control samples was significantly lower in samples of women with preeclampsia (p=0.001), in samples of women of the SGA group (p<0.0001), in samples of women of the trisomy 21 group (p=0.005), in samples of women of the trisomy 18 group (p=0.001) and in samples of women of the trisomy 13 group (p=0.004) (Table 2).

Multiparameter analysis for risk assessment of trisomy 21 for risk cut off 1 in 250 showed (Table 3) that the determination of pregnancy associated plasma protein A (PAPP-A), free beta hCG, PlGF and PlGF-2 was characterized by the lowest false positive rate of 4.8% compared to the FPR after the measurement of PAPP-A, free beta hCG (FPR: 9.6%) or after the measurement of PAPP-A, free beta hCG and PlGF (FPR: 9.6%).

Multiparameter analysis for risk assessment of trisomy 13 for risk cut off 1 in 250 showed (Table 4) that the determination of pregnancy associated plasma protein A (PAPP-A), free beta hCG, PlGF and PlGF-2 was characterized by the highest detection rate of 100% compared to the DR after the measurement of PAPP-A, free beta hCG (DR: 90%) or after the measurement of PAPP-A, free beta hCG and PlGF (DR: 90%).

Multiparameter analysis for risk assessment of preeclampsia showed (Table 5) that the determination of pregnancy associated plasma protein A (PAPP-A), pulsatile index (PI), mean arterial pressure (MAP), PlGF and PlGF-2 was characterized by the highest detection rate of 82% compared to the detection rate after the measurement of PAPP-A, PI, MAP (DR: 55%) or after the measurement of PAPP-A, PI, MAP and PlGF (DR: 77%).

Example 7

PlGF-2 in SGA and Preeclampsia Patients, $3^{rd}$ Trimester

PlGF-2 levels of preeclampsy and small for gestational age (SGA) patients in the $3^{rd}$ trimester of pregnancy were determined as described in Example 6. The patients' characteristics are shown in Table 6. The median MoM of PlGF-2 compared to control samples was significantly lower in samples of women with preeclampsia (p<0.0001) and in samples of women of the SGA group (p<0.0001) in the $3^{rd}$ trimester of pregnancy (Table 7).

Tables

TABLE 1

Characteristics in the study population.

| Characteristic | Normal (n = 295) | Early preeclampsia (n = 30) | Small for gestation (n = 30) | Trisomy 21 (n = 15) | Trisomy 18/13 (n = 20) |
| --- | --- | --- | --- | --- | --- |
| Maternal age in years, median (IQR) | 31.7 (27.2-35.7) | 32.7 (26.9-36.3) | 30.8 (24.4-85.2) | 38.1 (32.5-39.6)* | 34.9 (28.9-37.2) |
| Maternal weight in Kg, median (IQR) | 65.0 (58.0-73.0) | 73.8 (66.9-83.6)* | 69.8 (58.0-85.3) | 69.0 (63.0-74.0) | 67.1 (64.8-80.8) |
| Maternal height in cm, median (IQR) | 165 (160-170) | 162 (159-164)* | 162 (159-167) | 168 (163-169) | 164 (158-169) |
| Gestation at screening in weeks, median (IQR) | 12.7 (12.3-13.0) | 12.7 (12.3-13.0) | 12.6 (12.4-12.9) | 12.9 (12.1-13.7) | 12.4 (11.7-13.1) |
| Racial origin | | | | | |
| Caucasian, n (%) | 184 (62.4) | 12 (40.0) | 14 (46.7) | 9 (60.0) | 19 (95.0)* |
| Afro-Caribbean, n (%) | 81 (27.5) | 15 (50.0) | 14 (46.7) | 5 (33.3) | 1 (5.0) |
| South Asian, n (%) | 12 (4.1) | 2 (6.7) | 1 (3.3) | 1 (6.7) | 0 |
| East Asian, n (%) | 12 (4.1) | 1 (40.0) | 0 | 0 | 0 |
| Mixed, n (%) | 6 (2.0) | 0 | 1 (3.3) | 0 | 0 |

TABLE 1-continued

Characteristics in the study population.

| Characteristic | Normal (n = 295) | Early preeclampsia (n = 30) | Small for gestation (n = 30) | Trisomy 21 (n = 15) | Trisomy 18/13 (n = 20) |
|---|---|---|---|---|---|
| Nulliparous, n (%) | 150 (50.8) | 18 (60.0) | 19 (63.3) | 4 (26.7) | 7 (35.0) |
| Cigarette smoker, n (%) | 18 (6.1) | 2 (6.7) | 8 (26.7)* | 0 | 1 (5.0) |
| Conception | | | | | |
| Spontaneous, n (%) | 284 (96.3) | 28 (93.3) | 27 (90.0) | 9 (60.0)* | 19 (95.0) |
| Ovulation drugs, n (%) | 6 (2.0) | 0 | 1 (3.3) | 3 (20.0)* | 0 |
| In vitro fertilization, n (%) | 5 (1.7) | 2 (6.7) | 2 (6.7) | 3 (20.0)* | 1 (5.0) |

IQR = interquartile range

Comparison between outcome groups by Mann-Whitney U-test with post hoc Bonferroni correction and $\chi^2$-test or Fisher's exact test for categorical variables; Adjusted significance level P<0.01

TABLE 2

Comparison of median (interquartile range) of multiple of median (MoM) values of placental growth factor 2 of each adverse outcome group with the controls. Comparison between outcome groups by Mann-Whitney U-test with post hoc Bonferroni correction; Adjusted significance level P < 0.01*.

| Outcome group | Median PlGF-2 concentration (pg/ml) | Median MoM | Between outcome groups |
|---|---|---|---|
| Control (n = 295) | 151.9 | 1.038 (0.838-1.271) | — |
| Preeclampsia (n = 30) | 122.3 | 0.828 (0.590-1.047) | 0.001* |
| Small for gestational age (n = 30) | 128.7 | 0.751 (0.657-0.986) | <0.0001* |
| Trisomy 21 (n = 15) | 125.1 | 0.756 (0.689-1.051) | 0.005* |
| Trisomy 18 (n = 10) | 113.1 | 0.814 (0.710-0.933) | 0.001* |
| Trisomy 13 (n = 10) | 99.6 | 0.763 (0.645-0.963) | 0.004* |

TABLE 3

Detection rate (DR) and false positive rates (FPR) for risk assessment of aneuploidies using multiparameter analysis with different algorithms. Empirical results for Trisomy 21

| | 1 in 250 | |
|---|---|---|
| | FPR (%) | DR (%) |
| (i) maternal age, PAPP-A & free b-HCG | 9.6 | 86.7 |
| (ii) maternal age, PAPP-A, free b-HCG & PlGF | 9.6 | 93.3 |
| (iii) maternal age, PAPP-A, free b-HCG, PlGF & PlGF-2 | 4.8 | 93.3 |

TABLE 4

Detection rate (DR) and false positive rates (FPR) for risk assessment of aneuploidies using multiparameter analysis with different algorithms. Empirical results for Trisomy 13

| | 1 in 250 | |
|---|---|---|
| | FPR (%) | DR (%) |
| (i) maternal age, PAPP-A & free b-HCG | 0.3 | 90.0 |
| (ii) maternal age, PAPP-A, free b-HCG & PlGF | 0.7 | 90.0 |
| (iii) maternal age, PAPP-A, free b-HCG, PlGF & PlGF-2 | 0.3 | 100 |

TABLE 5

Detection rate (DR) and false positive rates (FPR) for risk assessment of preeclampsia using multiparameter analysis with different algorithms.

| Combination | 10$^{th}$ percentile | |
|---|---|---|
| | DR (%) | FPR (%) |
| PAPP-A + PI + MAP | 55 | 10 |
| PAPP-A + PI + MAP + PlGF | 77 | 10 |
| PAPP-A + PI + MAP + PlGF + PlGF-2 | 82 | 10 |

TABLE 6

Characteristics in the study population.

| Characteristic | Normal (n = 294) | Preeclampsia (n = 50) | Small for gestation (n = 99) |
|---|---|---|---|
| Maternal age in years, median (IQR) | 32.8 (29.0-35.4) | 34.2 (28.7-36.5) | 31.1 (25.6-35.1) |
| Maternal weight in Kg, median (IQR) | 74.0 (67.8-83.9) | 79.9 (72.5-89.9) | 69.0 (61.6-78.7) |
| Maternal height in cm, median (IQR) | 165 (160-168) | 164 (159-169) | 162 (157-166) |
| Gestation at screening in weeks, median (IQR) | 32.0 (32.0-32.3) | 32.0 (32.0-32.3) | 32.0 (32.0-32.3) |

TABLE 6-continued

Characteristics in the study population.

| Characteristic | Normal (n = 294) | Preeclampsia (n = 50) | Small for gestation (n = 99) |
|---|---|---|---|
| Racial origin | | | |
| Caucasian, n (%) | 181 (61.6) | 31 (62.0) | 54 (54.5) |
| Afro-Caribbean, n (%) | 70 (23.8) | 14 (28.0) | 33 (33.3) |
| South Asian, n (%) | 19 (6.5) | 2 (4.0) | 6 (6.1) |
| East Asian, n (%) | 14 (4.8) | 2 (4.0) | 2 (2.0) |
| Mixed, n (%) | 10 (3.4) | 1 (2.0) | 4 (4.0) |
| Nulliparous, n (%) | 159 (54.1) | 33 (66.0) | 68 (68.7) |
| Cigarette smoker, n (%) | 8 (2.7) | 3 (6.0) | 18 (18.2) |
| Conception | | | |
| Spontaneous, n (%) | 277 (94.2) | 47 (94.0) | 94 (94.9) |
| Ovulation drugs, n (%) | 5 (1.7) | 0 | 0 |
| In vitro fertilization, n (%) | 12 (4.1) | 3 (6.0) | 5 (5.1) |

Values are presented as medians (IQR = interquartile range) or numbers (%).

TABLE 7

Comparison of median (interquartile range) of multiple of median (MoM) values of placental growth factor 2 of each adverse outcome group with the controls at 3rd trimester. Comparison between outcome groups by Mann-Whitney U-test; Adjusted significance level $P < 0.01$*.

| Outcome group | Median PlGF-2 concentration (pg/ml) | Median MoM | Between outcome groups |
|---|---|---|---|
| Control (n = 294) | 1408.5 | 1.005 (0.622-1.390) | — |
| Preeclampsia (n = 50) | 687.9 | 0.481 (0.358-0.763) | <0.0001* |
| Small for gestational age (n = 99) | 881.2 | 0.622 (0.398-1.016) | <0.0001* |

The invention claimed is:

1. A method for the diagnosis, prognosis, risk assessment, and/or risk stratification of preeclampsia, or the risk of delivery of a child with an aneuploidy, or the risk of delivery of a small for gestational age neonate in a pregnant female subject, comprising an immunoassay method for the detection of placental growth factor 2 (PlGF-2) comprising:
   (a) contacting a sample suspected of comprising PlGF-2 with a first antibody or an antigen-binding fragment thereof specific for PlGF and a second antibody or an antigen-binding fragment thereof, specific for PlGF-2 under conditions allowing for the formation of a ternary complex between PlGF-2 and the two antibodies or antigen-binding fragments thereof,
      wherein the first antibody is an antibody provided by R&D Systems Europe Ltd. Abingdon UK under Ref. No.: AF-264-PB (polyclonal anti-PlGF antibody),
   wherein the second antibody is the antibody which is produced by a hybridoma cell line selected from the group consisting of the cell line 477/G2 deposited as DSM ACC3222 and the cell line 477/ES deposited as DSM ACC3221;
   (b) detecting the binding of the two antibodies or antigen-binding fragments thereof to PlGF-2;
   (c) determining the level of placental growth factor 2 (PlGF-2) in a sample from the subject; and
   (d) comparing the determined level in the sample to a control level of PlGF-2 derived from subjects without preeclampsia, or the risk of delivery of a child with an aneuploidy, or the risk of delivery of a small for gestational age neonate;
      wherein a decreased level of PlGF-2 in the sample from the subject as compared to the control level is indicative for preeclampsia, increased risk of acquiring preeclampsia, increased risk of aggravation of preeclampsia, increased risk of delivery of a child with an aneuploidy, increased risk of an aggravation of the risk of delivery of a child with an aneuploidy, increased risk of delivery of a small for gestational age neonate, and/or increased risk of an aggravation of the risk of delivery of a small for gestational age neonate.

2. The method for diagnosing preeclampsia or the risk of delivery of a child with an aneuploidy or the risk of delivery of a small for gestational age neonate in the pregnant female subject of claim 1, wherein the level of placental growth factor 2 (PlGF-2) is determined in a sample from the subject to be diagnosed and wherein a level of PlGF-2 below a "multiple of the median" (MoM) of 0.85 of the control group is indicative for the prenatal disorder or condition.

3. The method of claim 1, wherein said subject is in the first trimester of pregnancy.

4. The method of claim 1, wherein at least one further parameter relevant for diagnosis of preeclampsia is determined in the sample, optionally wherein
   (a) the disorder or condition is preeclampsia and the further parameter preeclampsia is one or more selected from the group consisting of PAPPA, ultrasound markers (Pulsatile-Index, diastolic notching), Mean Arterial Pressure, PlGF, sFlt, maternal history, soluble Endoglin (sEng), inhibin A, activin A, vascular endothelial growth factor (VEGF), human chorionic gonadotrophin (hCG) and cell free fetal DNA,
   (b) the disorder or condition is aneuploidy and the further parameter is one or more selected from the group consisting of PAPP-A, free-beta hCG, nuchal translucency, maternal age, AFP, PlGF, fetal nasal bone, biparietal diameter/nasal bone ratio, hCG, inhibin A, unconjugated estriol 3 (uE3), and cell free fetal DNA, or
   (c) the disorder or condition is small for gestational age and the further parameter is one or more selected from the group consisting of PAPP-A, maternal history, PlGF, sFlt, AFP, free-beta hCG, hCG, inhibin-A, activin A, sEng, symphysis-fundal height (SFH), fetal biometry (femur length (FL), head circumference (HC), biparietal diameter (BPD), abdominal circumference (AC)) and ultrasound markers (Pulsatile-Index, Umbilical artery Doppler, Middle cerebral artery Doppler, Ductus venosus Doppler).

5. A method for the diagnosis, prognosis, risk assessment, and/or risk stratification of preeclampsia, or the risk of delivery of a child with an aneuploidy, or the risk of delivery of a small for gestational age neonate in a pregnant female subject, comprising an immunoassay method for the detection of placental growth factor 2 (PlGF-2) comprising:
   (a) contacting a sample suspected of comprising PlGF-2 with a first antibody or an antigen-binding fragment thereof specific for PlGF and a second antibody or an antigen-binding fragment thereof, specific for PlGF-2,
      wherein the first antibody is an antibody provided by R&D Systems Europe Ltd. Abingdon UK under Ref. No.: AF-264-PB (polyclonal anti-PlGF antibody), wherein the second antibody is the antibody produced by a hybridoma cell line selected from the group consisting of the cell line 477/G2 deposited as DSM ACC3222 and the cell line 477/ES deposited as DSM ACC3221;

(b) detecting the binding of the two antibodies or antigen-binding fragments thereof to PlGF-2;

(c) determining the level of placental growth factor 2 (PlGF-2) in a sample from the subject; and (d) comparing the determined level in the sample to a control level of PlGF-2 derived from subjects without preeclampsia, or the risk of delivery of a child with an aneuploidy, or the risk of delivery of a small for gestational age neonate;

wherein a decreased level of PlGF-2 in the sample from the subject as compared to the control level is indicative for preeclampsia, increased risk of acquiring preeclampsia, increased risk of aggravation of preeclampsia, increased risk of delivery of a child with an aneuploidy, increased risk of an aggravation of the risk of delivery of a child with an aneuploidy, increased risk of delivery of a small for gestational age neonate, and/or increased risk of an aggravation of the risk of delivery of a small for gestational age neonate.

* * * * *

SEQUENCE LISTING

```
<160> NUMBER OF SEQ ID NOS: 7

<210> SEQ ID NO 1
<211> LENGTH: 242
<212> TYPE: PRT
<213> ORGANISM: Homo sapiens
<220> FEATURE:
<221> NAME/KEY: MISC_FEATURE
<222> LOCATION: (1)..(242)
<223> OTHER INFORMATION: Precursors of PlGF (PGF) isoforms (canonical
      sequence)

<400> SEQUENCE: 1

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110
```

```
Asp Arg Pro Ser Tyr Val Glu Leu Thr Phe Ser Gln His Val Arg Cys
            115                 120                 125

Glu Cys Arg His Ser Pro Gly Arg Gln Ser Pro Asp Met Pro Gly Asp
    130                 135                 140

Phe Arg Ala Asp Ala Pro Ser Phe Leu Pro Pro Arg Arg Ser Leu Pro
145                 150                 155                 160

Met Leu Phe Lys Met Glu Trp Gly Cys Ala Leu Thr Gly Ser Gln Ser
                165                 170                 175

Ala Val Trp Pro Ser Ser Pro Val Pro Glu Glu Ile Pro Arg Met His
            180                 185                 190

Pro Gly Arg Asn Gly Lys Lys Gln Gln Arg Lys Pro Leu Arg Glu Lys
        195                 200                 205

Met Lys Pro Glu Arg Arg Pro Lys Gly Arg Gly Lys Arg Arg Arg
    210                 215                 220

Glu Lys Gln Arg Pro Thr Asp Cys His Leu Cys Gly Asp Ala Val Pro
225                 230                 235                 240

Arg Arg

<210> SEQ ID NO 2
<211> LENGTH: 131
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: Mature PlGF-1

<400> SEQUENCE: 2

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 3
<211> LENGTH: 152
<212> TYPE: PRT
<213> ORGANISM: Homo sapiens
<220> FEATURE:
<221> NAME/KEY: MISC_FEATURE
<222> LOCATION: (1)..(152)
<223> OTHER INFORMATION: Mature PlGF-2

<400> SEQUENCE: 3

Leu Pro Ala Val Pro Pro Gln Gln Trp Ala Leu Ser Ala Gly Asn Gly
1               5                   10                  15
```

```
Ser Ser Glu Val Glu Val Val Pro Phe Gln Glu Val Trp Gly Arg Ser
        20                  25                  30

Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
    50                  55                  60

Cys Thr Gly Cys Cys Gly Asp Glu Asp Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Arg Pro Lys Gly
        115                 120                 125

Arg Gly Lys Arg Arg Glu Lys Gln Arg Pro Thr Asp Cys His Leu
    130                 135                 140

Cys Gly Asp Ala Val Pro Arg Arg
145                 150

<210> SEQ ID NO 4
<211> LENGTH: 203
<212> TYPE: PRT
<213> ORGANISM: Homo sapiens
<220> FEATURE:
<221> NAME/KEY: MISC_FEATURE
<222> LOCATION: (1)..(203)
<223> OTHER INFORMATION: Mature PlGF-3

<400> SEQUENCE: 4

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
        20                  25                  30

Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg His Ser Pro Gly Arg Gln Ser Pro Asp Met Pro Gly Asp Phe Arg
        115                 120                 125

Ala Asp Ala Pro Ser Phe Leu Pro Pro Arg Arg Ser Leu Pro Met Leu
    130                 135                 140

Phe Arg Met Glu Trp Gly Cys Ala Leu Thr Gly Ser Gln Ser Ala Val
145                 150                 155                 160

Trp Pro Ser Ser Pro Val Pro Glu Glu Ile Pro Arg Met His Pro Gly
                165                 170                 175

Arg Asn Gly Lys Lys Gln Gln Arg Lys Pro Leu Arg Glu Lys Met Lys
            180                 185                 190

Pro Glu Arg Cys Gly Asp Ala Val Pro Arg Arg
        195                 200
```

```
<210> SEQ ID NO 5
<211> LENGTH: 224
<212> TYPE: PRT
<213> ORGANISM: Homo sapiens
<220> FEATURE:
<221> NAME/KEY: MISC_FEATURE
<222> LOCATION: (1)..(224)
<223> OTHER INFORMATION: Mature PlGF-4

<400> SEQUENCE: 5

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg His Ser Pro Gly Arg Gln Ser Pro Asp Met Pro Gly Asp Phe Arg
        115                 120                 125

Ala Asp Ala Pro Ser Phe Leu Pro Pro Arg Arg Ser Leu Pro Met Leu
130                 135                 140

Phe Arg Met Glu Trp Gly Cys Ala Leu Thr Gly Ser Gln Ser Ala Val
145                 150                 155                 160

Trp Pro Ser Ser Pro Val Pro Glu Glu Ile Pro Arg Met His Pro Gly
                165                 170                 175

Arg Asn Gly Lys Lys Gln Gln Arg Lys Pro Leu Arg Glu Lys Met Lys
            180                 185                 190

Pro Glu Arg Arg Arg Pro Lys Gly Arg Gly Lys Arg Arg Arg Glu Lys
        195                 200                 205

Gln Arg Pro Thr Asp Cys His Leu Cys Gly Asp Ala Val Pro Arg Arg
    210                 215                 220

<210> SEQ ID NO 6
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: Heparin binding domain

<400> SEQUENCE: 6

Arg Arg Pro Lys Gly Arg Gly Lys Arg Arg Arg Glu Lys Gln Arg Pro
1               5                   10                  15

Thr Asp Cys His Leu
            20

<210> SEQ ID NO 7
<211> LENGTH: 72
<212> TYPE: PRT
<213> ORGANISM: Homo sapiens
<220> FEATURE:
<221> NAME/KEY: MISC_FEATURE
```

<222> LOCATION: (1)..(72)
<223> OTHER INFORMATION: loop 3

<400> SEQUENCE: 7

His Ser Pro Gly Arg Gln Ser Pro Asp Met Pro Gly Asp Phe Arg Ala
1               5                   10                  15

Asp Ala Pro Ser Phe Leu Pro Pro Arg Arg Ser Leu Pro Met Leu Phe
            20                  25                  30

Arg Met Glu Trp Gly Cys Ala Leu Thr Gly Ser Gln Ser Ala Val Trp
        35                  40                  45

Pro Ser Ser Pro Val Pro Glu Glu Ile Pro Arg Met His Pro Gly Arg
    50                  55                  60

Asn Gly Lys Lys Gln Gln Arg Lys
65                  70